(12) United States Patent
Johansen et al.

(10) Patent No.: US 7,589,869 B2
(45) Date of Patent: Sep. 15, 2009

(54) ADJUSTING IMAGE QUALITY USING MULTI-WAVELENGTH LIGHT

(75) Inventors: Brian Johansen, Hillsboro, OR (US); Mehmet E. Alpay, Portland, OR (US)

(73) Assignee: Electro Scientific Industries, Inc., Portland, OR (US)

( * ) Notice: Subject to any disclaimer, the term of this patent is extended or adjusted under 35 U.S.C. 154(b) by 382 days.

(21) Appl. No.: 11/414,678

(22) Filed: Apr. 28, 2006

(65) Prior Publication Data

US 2007/0253033 A1    Nov. 1, 2007

(51) Int. Cl.
*H04N 1/04* (2006.01)
(52) U.S. Cl. .................. 358/448; 358/474; 358/475
(58) Field of Classification Search ............. 358/448, 358/475, 474; 382/141, 144–147
See application file for complete search history.

(56) References Cited

U.S. PATENT DOCUMENTS

| | | | |
|---|---|---|---|
| 5,737,122 A | 4/1998 | Wilt et al. ................. 359/436 |
| 6,259,827 B1 * | 7/2001 | Nichani ..................... 382/291 |
| 6,396,949 B1 * | 5/2002 | Nichani ..................... 382/173 |
| 6,587,582 B1 * | 7/2003 | Nichani et al. ............. 382/149 |
| 6,870,949 B2 | 3/2005 | Baldwin .................... 382/145 |
| 2005/0264813 A1 * | 12/2005 | Giakos ...................... 356/369 |
| 2007/0108284 A1 * | 5/2007 | Pankow et al. ............. 235/454 |

* cited by examiner

*Primary Examiner*—Houshang Safaipour
(74) *Attorney, Agent, or Firm*—Young Basile

(57) ABSTRACT

A method and apparatus to improve image quality in images captured via monochromatic cameras using multi-wavelength lighting. A contrast optimization algorithm determines which particular wavelength among those available is most suitable to maximize contrast. The quality of the image can be further improved through active noise cancellation by determining the lighting schemes that provide maximum and minimum contrast between a target and a background. The elimination of image texture data (i.e., noise) is then accomplished through pixel-by-pixel division of the maximum by the minimum contrast image. Alternatively, images obtained using at least two wavelengths can be algebraically combined for noise reduction. The resulting composite image can be fed into any known target identification algorithm.

16 Claims, 14 Drawing Sheets

| LIGHTING SCHEME | BACKGROUND AVERAGE PIXEL VALUE | TARGET AVERAGE PIXEL VALUE | CONTRAST METRIC |
|---|---|---|---|
| BLUE LEDS | 246.9604 | 144.1300 | 0.2629 |
| GREEN LEDS | 101.7078 | 63.2830 | 0.2329 |
| RED LEDS | 118.2418 | 119.6117 | 0.0058 |
| IR LEDS | 81.2057 | 125.7639 | 0.2153 |

FIG. 10

ADJUSTING IMAGE QUALITY USING MULTI-WAVELENGTH LIGHT

TECHNICAL FIELD

This invention relates in general to a method for improving image quality in images captured via monochromatic cameras.

BACKGROUND

There is a class of semiconductor products that are predominantly planar and specular (flat and shiny), and it is frequently necessary to image these devices in such way that even minor deviations from planar and specular are imaged with adequate contrast. One such class of products includes semiconductor wafers that may be provided with indicia indicating, among other things, wafer number and manufacturer. These indicia are defects in the surface of the wafer and are typically a matrix of laser etched pits. They are commonly known in the art as "soft marks" or "fiducial markers." It is necessary to image these marks to read the codes at various steps along the manufacturing process.

Another class of products that are routinely processed using laser-power material removal schemes includes dielectric-coated conducting metal substrates used as chip carriers for semiconductor devices or as printed wiring boards for electronic devices. These, too, are predominantly planar and specular (flat and shiny), and it is frequently necessary to image these devices in such way that surface and/or subsurface features can be imaged with adequate contrast. One such class of products includes semiconductor chip carriers that may be provided with indicia indicating, among other things, process datums. These indicia are generally conducting metal (commonly copper or a copper alloy) on or beneath of the surface of the workpiece and are typically round, square or another geometric shape created by chemical etching the metal conducting layer during earlier processing step(s). But, these indicia could include mechanically drilled or punched holes through the entirety of the workpiece. They are commonly known in the art as "tooling holes," "fiducial marks," or simply "alignment targets." It is necessary to image these marks to align and scale the workpiece to the machine at various steps along the manufacturing process.

After the devices have been processed (generally cut by saw into individual rectangular devices), it may be necessary to inspect the edges for small chips and cracks that may propagate over time and cause premature device failure or to inspect the laser-processed features for cosmetic or functional reasons. These inspection processes are automated and use electronic imaging cameras in combination with digital electronic computers that are programmed to perform the necessary inspections, measurements and identifications.

To properly image these objects, including highlighting these very minor features, a number of lighting systems and cameras have been used. For example, commonly assigned U.S. Pat. No. 5,737,122 entitled Illumination System for OCR of Indicia on a Substrate, which is incorporated herein in its entirety by reference. The '122 patent describes a system wherein the axis of the camera and the axis of the lighting module are at complimentary acute angles symmetric about the normal to a specular object. The narrow-angle dark field lights are positioned close to the optical axis and are prevented from being directly imaged by the camera by baffles placed in the imaging path to prevent this. The position of the baffles restricts the field of view of the imager, but this is considered an acceptable compromise.

In another example, commonly assigned U.S. Pat. No. 6,870,949 discloses a coaxial narrow angle dark field imaging system that utilizes a telecentric lens to illuminate objects with symmetric coaxial narrow angle dark field illumination. The illumination technique is particularly suited to highlight minor features or defects on planar specular objects. In particular, the coaxial light source directs light rays towards a telecentric lens which redirects the light rays towards the substantially planar specular object. The light rays are reflected back through the telecentric lens towards a camera. To the extent that the light rays are reflected from a planar specular portion of the object the light rays are blocked by a telecentric stop. Light rays reflected from a defect or feature in the planar specular object will pass through an aperture in the stop to a camera. U.S. Pat. No. 6,870,949 is also incorporated herein in its entirety by reference.

With these and other systems, images are obtained using monochromatic cameras are typically shown in grey-scale. Lights used are white or monochromatic lights, such as white or single wavelength LEDs. Using these images, automatic identification of fiducial markers on a work piece for inspection and part alignment purposes is a well-established practice in the machining industry. Various algorithms have already been developed and are readily in use to process the images for this identification. Regardless of how sophisticated an algorithm is, however, a "good" image with a high level of contrast between the target and the surrounding background is still critical to its success.

SUMMARY OF THE INVENTION

The method and apparatus disclosed herein improves image quality by improving image contrast in images captured via monochromatic cameras. These improved images can be fed into a target identification routine or algorithm to determine the identification of marks on a surface, including but not limited to indicia.

A method to improve image quality in images of a surface captured via monochromatic cameras taught herein includes, for example, using multi-wavelength lighting to obtain a plurality of images and optimizing contrast between portions of the surface based on the plurality of images.

An apparatus to improve image quality in images of a surface captured via a monochromatic camera taught herein includes, for example, means for using multi-wavelength lighting to obtain a plurality of images and means for optimizing contrast between portions of the surface based on the plurality of images.

These and other unique features of the invention are discussed in further detail hereinbelow.

BRIEF DESCRIPTION OF THE DRAWING

The application file contains at least one drawing executed in color. Copies of this patent application publication with color drawings will be provided by the Office upon request and payment of the necessary fee. The gray-scale drawings are necessary to discern the individual pixels and to illustrate contrast between pixels in the images.

FIG. 10 is a table that compares the average background pixel values, target pixel values and contrast metrics for the four raw images provided in FIGS. 8A-8D.

DETAILED DESCRIPTION OF THE PREFERRED EMBODIMENTS

Improved image contrast and target identification quality in images captured via monochromatic cameras can be achieved with the present invention. Generally, a contrast optimization algorithm using multi-wavelength lighting is performed. The maximum contrast can be obtained by utilizing a single wavelength using a procedure for determining which particular wavelength among the ones available in the lighting system would be most suitable. Second, the quality of the image that will be fed into the target identification routine can be further improved through active noise cancellation by employing the contrast optimization algorithm to determine the lighting schemes that provides maximum and minimum contrast between a target and a background. The desired elimination of image texture data (i.e., noise) can then be accomplished through pixel-by-pixel division of the maximum contrast image by the minimum contrast image. Third, a synthetic image with high contrast between the target and background can be created by subtracting images of the area of interest illuminated by two or more individual wavelengths. The resulting composite image can then be fed into any one of a number of known target identification algorithms.

Any known image acquisition system comprising generally a controller, camera(s) and a lighting system can be used according to the description herein. The algorithms described herein can be programmed into and can be performed by the standard controller or can be performed by a general purpose microprocessor coupled to memory storing the algorithms or by a microcontroller with on-board memory as is known in the art.

Details are best described by first developing a mathematical model for contrast between the target, e.g., indicia, and background on an image. The following definitions are used. The spectral response G ($\lambda$) of the monochromatic camera is defined as the camera's quantum efficiency as a function of incident light wavelength. Second, the reflection spectrum H ($\lambda$) of a flat surface is defined as the normalized spectrum of the reflections from that surface when the surface is illuminated by a flat spectrum light source (i.e., one that provides a consistent level of illumination over the rage of wavelengths to which the camera/lens system responds and focuses properly.

Figure 1:
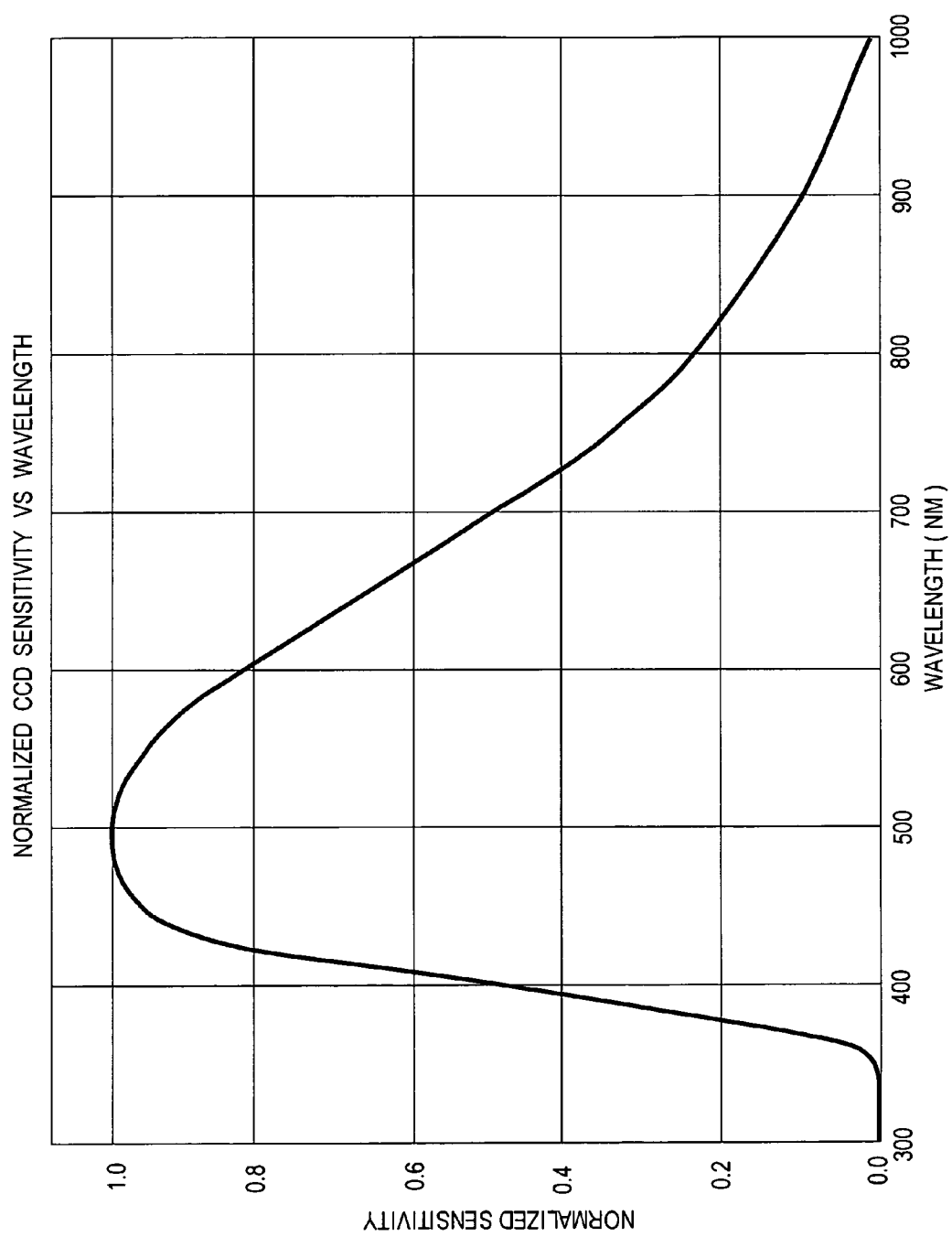
FIG. 1 is an example of the spectral response of a typical monochromatic CCD camera.
Figure 2:
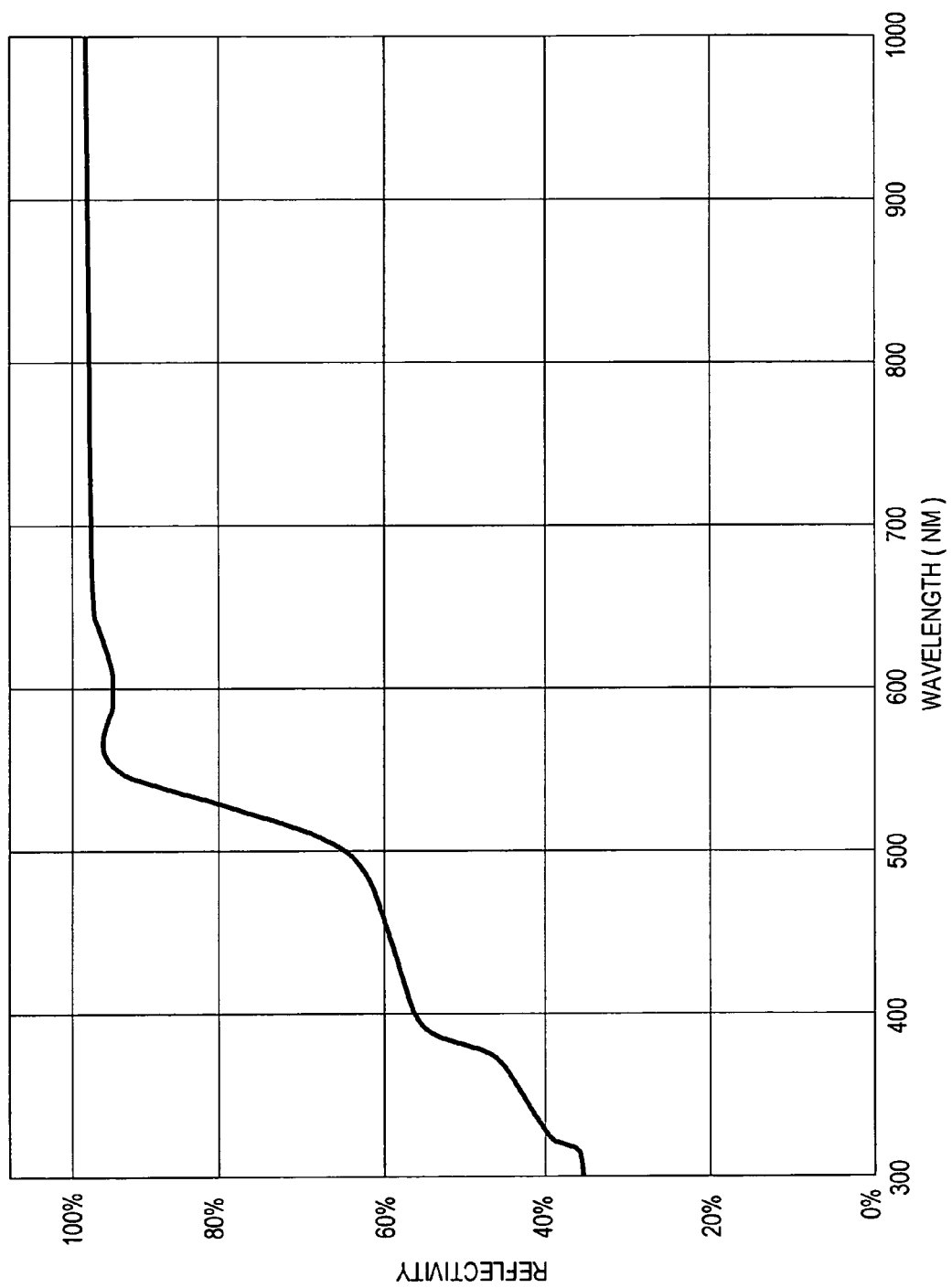
FIG. 2 is an example of reflectivities of a target area $H_T(\lambda)$.
Figure 3:
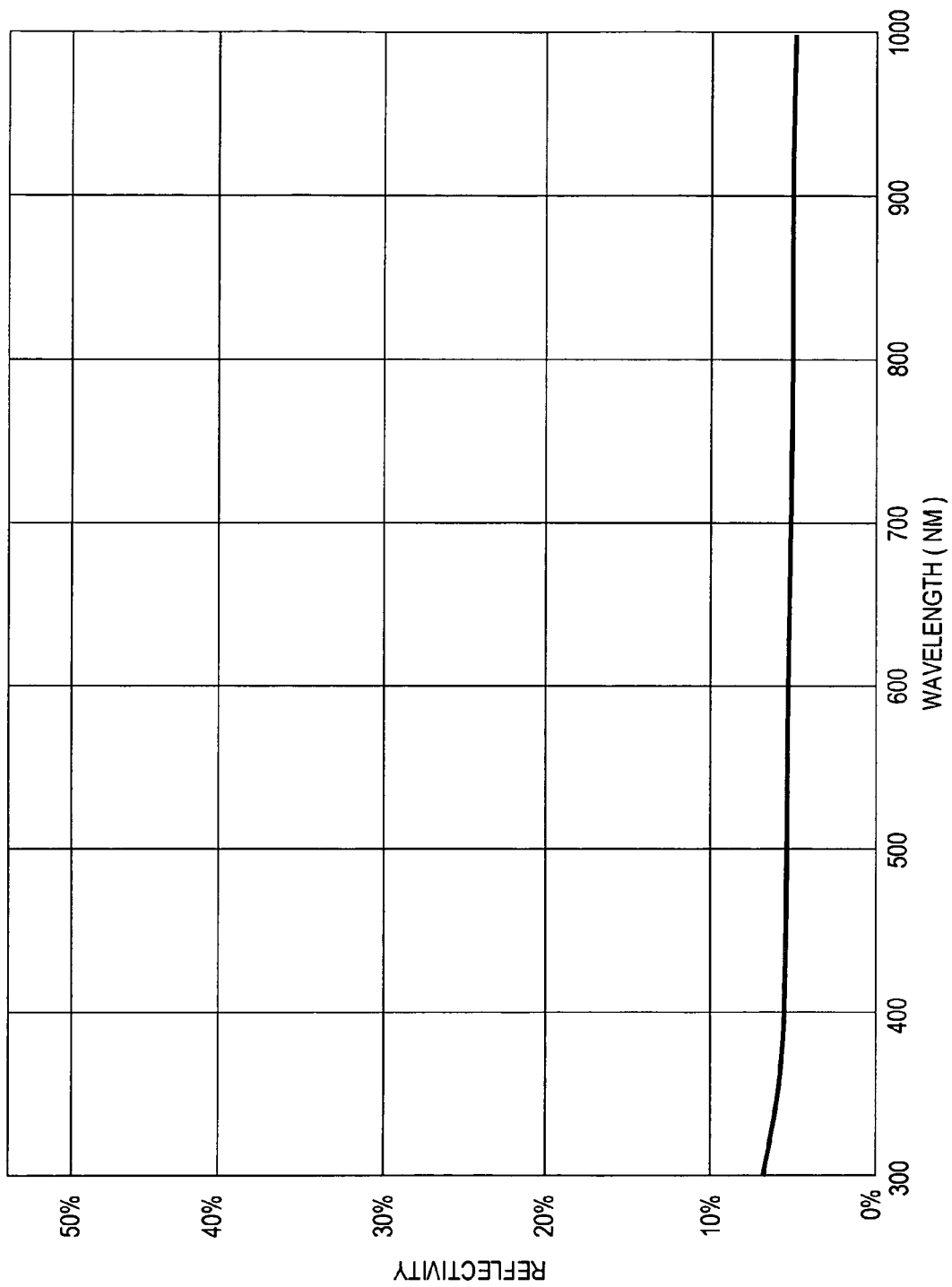
FIG. 3 is an example of reflectivities of a background area $H_B(\lambda)$.

FIG. 1 is an example of the spectral response of a typical monochromatic charge-coupled device (CCD) camera. FIGS. 2 and 3 are examples of reflectivities of example target and background areas ($H_T(\lambda)$ and $H_B(\lambda)$), respectively. Note that FIG. 2 shows the normal incidence reflectivity of copper versus wavelength as copper is a common target as described above. The example background is RCF resin so in FIG. 3 the normal incidence reflectivity of RCF resin versus wavelength is shown.

Assume that there exists N different light sources corresponding to wavelengths $\lambda_k$, where k=1, ..., N. The spectral response $F_k(\lambda)$ of the k'th light source is given by equation (1) below:

$$F_k(\lambda) = \alpha_k \delta(\lambda - \lambda_k); \tag{1}$$

where $\alpha_k$ denotes the intensity of the k'th light source and $\delta$ denotes the Dirac-Delta function. Assuming a spatially uniform target, the camera output for a pixel in the target area ($Cout_T$) is given by:

$$\begin{aligned}Cout_T &= \int_\alpha^\infty G(\lambda) H_T(\lambda) \left( \sum_{k=1}^N F_k(\lambda) \right) d\lambda \\ &= \sum_{k=1}^N \alpha_k \int_{\lambda=0}^\infty G(\lambda) H_T(\lambda) \delta(\lambda - \lambda_k) d\lambda \\ &= \sum_{k=1}^N \alpha_k G(\lambda_k) H_T(\lambda_k).\end{aligned} \tag{2}$$

Note that equation (2) assumes that the camera output is not saturated. In a similar manner, the camera output for the background area ($Cout_B$) is given by:

$$Cout_B = \sum_{k=1}^N \alpha_k G(\lambda_k) H_B(\lambda_k). \tag{3}$$

This also assumes that the camera output is not saturated.

Now, one can define a "contrast metric" ($C_M$) according to equation (4):

$$C_M = \frac{|Cout_T - Cout_B|}{Cout_T + Cout_B}. \tag{4}$$

There are a number of important features of the contrast metric $C_M$ defined above. First, the metric is invariant to global changes in overall intensity. Generally, changing the relative intensities of all light sources by the same factor will not change the image contrast. This is consistent with common sense; one would not expect the true contrast in a grey-scale image to improve by simply multiplying each pixel value by a constant factor. Note also that this definition implies that one should use a "normalized" algorithm for target identification such as normalized correlation as is known in the art. One could also apply histogram equalization to all captured images before employing the target identification method of choice.

A second important feature is that the contrast metric $C_M$ is symmetric with respect to the target and background. That is, swapping what is deemed "target" and what is deemed "background" will leave the contrast metric $C_M$ unchanged. This is also quite consistent with common sense as the phrase "contrast between target and background" is commonly understood by those skilled in the art. A "target" that has a high contrast with respect to a "background" automatically implies a background that has a high contrast with respect to the target.

A third important feature of the contrast metric $C_M$ is that its maximum value is one (1). This is achieved when the camera response to either the target or the background is identically zero. With proper scaling of overall intensity this scenario corresponds to a perfect black target against a white background, or vice versa. The fact that the metric yields the highest contrast in this particular case is again quite in line with common sense.

Given the observations above, the contrast metric $C_M$ as defined in equation (4) above is an appropriate tool for the analysis described herein.

Substituting the expressions for $Cout_T$ and $Cout_B$ from equations (2) and (3) in equation (4), one then obtains the following equation (5) for the contrast metric $C_M$:

$$C_M = \frac{\left|\sum_{k=1}^{N} \alpha_k G(\lambda_k) H_T(\lambda_k) - \sum_{k=1}^{N} \alpha_k G(\lambda_k) H_B(\lambda_k)\right|}{\sum_{k=1}^{N} \alpha_k G(\lambda_k) H_T(\lambda_k) + \sum_{k=1}^{N} \alpha_k G(\lambda_k) H_B(\lambda_k)};$$

$$= \frac{\left|\sum_{k=1}^{N} \alpha_k G(\lambda_k)[H_T(\lambda_k) - H_B(\lambda_k)]\right|}{\sum_{k=1}^{N} \alpha_k G(\lambda_k)[H_T(\lambda_k) + H_B(\lambda_k)]};$$

$$= \frac{\left|\sum_{k=1}^{N} \alpha_k [\Gamma_k^T - \Gamma_k^B]\right|}{\sum_{k=1}^{N} \alpha_k [\Gamma_k^T + \Gamma_k^B]};$$

where $\Gamma_k^T = G(\lambda_k) H_T(\lambda_k)$ and $\Gamma_k^B = G(\lambda_k) H_B(\lambda_k)$ After defining the saturation level of the camera as $Cout_{MAX}$, one is now ready to pose the contrast optimization problem in precise mathematical terms. For a given set of $\Gamma_k^T$, $\Gamma_k^B \in \mathfrak{R}^+$ (k=1, ..., N), $\alpha_k$ is found that maximizes equation (5) subject to the following constraints:

$$\alpha_k \geq 0;$$

$$\sum_{k=1}^{N} \alpha_k \Gamma_k^T \leq Cout_{MAX}; \text{ and}$$

$$\sum_{k=1}^{N} \alpha_k \Gamma_k^B \leq Cout_{MAX}.$$

At first glance, solving this contrast optimization problem appears difficult. However, a few observations lead to a simple algorithm to address the problem. First, the constraints on $\alpha_k$ create a convex set of feasible solutions bounded by N+2 hyper-planes: $\alpha_k=0$, k=1, ..., N; $\Gamma_{k=1}^N \alpha_k \Gamma_k^T = Cout_{MAX}$; and $$\sum_{k=1}^{N} \alpha_k \Gamma_k^B = Cout_{MAX}.$$

These last two hyper-planes are referred to herein as the "saturation hyper-planes."

Second, an optimal solution exists on a surface that corresponds to one of the N+2 hyper-planes that form the boundaries of the set of feasible solutions. This is a direct result of the fact that the contrast metric $C_M$ is invariant to changes in overall intensity as described previously. Assume, for example, that there is an optimal solution $\alpha_k^*$ that is not on a boundary surface. In this case, one could then simply scale all $\alpha_k^*$ with the appropriate gain factor $\gamma$ so that $\gamma \alpha_k^*$ lies on a boundary surface. Since such an overall scaling of intensity does not change the contrast metric $C_M$, the solution $\gamma \alpha_k^*$ would yield the same optimal contrast metric as the original solution and hence be an optimal solution itself.

With a conclusion that an optimal solution will exist on a boundary surface, additional observations can be made. A third observation is that the solution will not be along the hyper-line that forms the intersection between the saturation hyper-planes. The reason is that along this line the contrast metric would be zero, which cannot be an optimal (maximum) solution. Fourth, it can be shown that the optimal solution cannot lie in the middle of either one of the boundary surfaces formed by the saturation hyper-planes. For any such feasible solution, one can show mathematically that there is a better solution by moving the solution point in the proper direction while staying on that surface. The existence of this better solution implies that the original solution could not have been optimal one.

Putting together all these observations, the optimal solution has to be at one of the "corners" formed by the intersection of one of the two saturation hyper-planes with N−1 of the $\alpha_k=0$, k=1, ..., N hyper-planes. This means that the optimal solution will have the form of equation (6) below.

$$\alpha_k^* = \begin{cases} \alpha_n, & \text{if } k = n \\ 0, & \text{if } k \neq n \end{cases} \quad (6)$$

This equation not only provides a simple algorithm to determine the lighting configuration that will yield the optimal contrast, it also provides an important insight to the problem. Namely, the maximum contrast is obtained with only one of the N light sources active. The implications of this observation are discussed in more detail hereinbelow.

Next, an algorithm for determining the lighting condition under which a maximum contrast as defined by the contrast metric $C_M$ of equation (4) is achieved. For each k=1, ..., N, the corresponding single-source contrast $C_{M,k}$ is found as follows.

$$C_{M,k} = \frac{|\alpha_k(\Gamma_k^T - \Gamma_k^B)|}{\alpha_k(\Gamma_k^T + \Gamma_k^B)};$$

$$= \frac{|(\Gamma_k^T - \Gamma_k^B)|}{(\Gamma_k^T + \Gamma_k^B)}.$$

Then, the wavelength $\lambda_k$ that corresponds to the largest $C_{M,k}$ value calculated in the previous step is chosen and used to illuminate the surface.

Note that the above algorithm does not specify the absolute value of the intensity $\alpha_k$ to be used for maximum contrast. This again is consistent with the mathematical definition of the contrast metric $C_M$, which is invariant to overall intensity levels. For practical implementations, however, setting $\alpha_k$ to its maximum permissible value of:

$$\alpha_k = \min\{\text{Cout}_{MAX}/\Gamma_k^T, \text{Cout}_{MAX}/\Gamma_k^B\}$$

will improve the signal to quantization noise ratio in the raw image, i.e., the image captured by the monochromatic camera prior to optimization.

For an example of the above algorithm in practice, assume a target and background of a surface are illuminated via red, green and blue (RGB) lighting and the following $\Gamma$ values are observed:

$$\Gamma_R^T = 5, \Gamma_R^B = 2;$$

$$\Gamma_G^T = 3, \Gamma_G^B = 5; \text{ and}$$

$$\Gamma_B^T = 8, \Gamma_B^B = 5.$$

Employing the teachings herein, one obtains the following contrast metric values for individual (red-only, green-only, and blue-only) light schemes:

$$C_{M,R} = |5-2|/(5+2) = 3/7;$$

$$C_{M,G} = |3-5|/(3+5) = 2/8; \text{ and}$$

$$C_{M,B} = |8-5|/(8+5) = 3/13.$$

In this particular example the red-only lighting will yield the highest contrast between the background and the target. If $\text{Cout}_{MAX}$ is 255, then the corresponding intensity factor $\alpha_R$ should be set to $\alpha_R = 255/5 = 51$.

Figure 4:
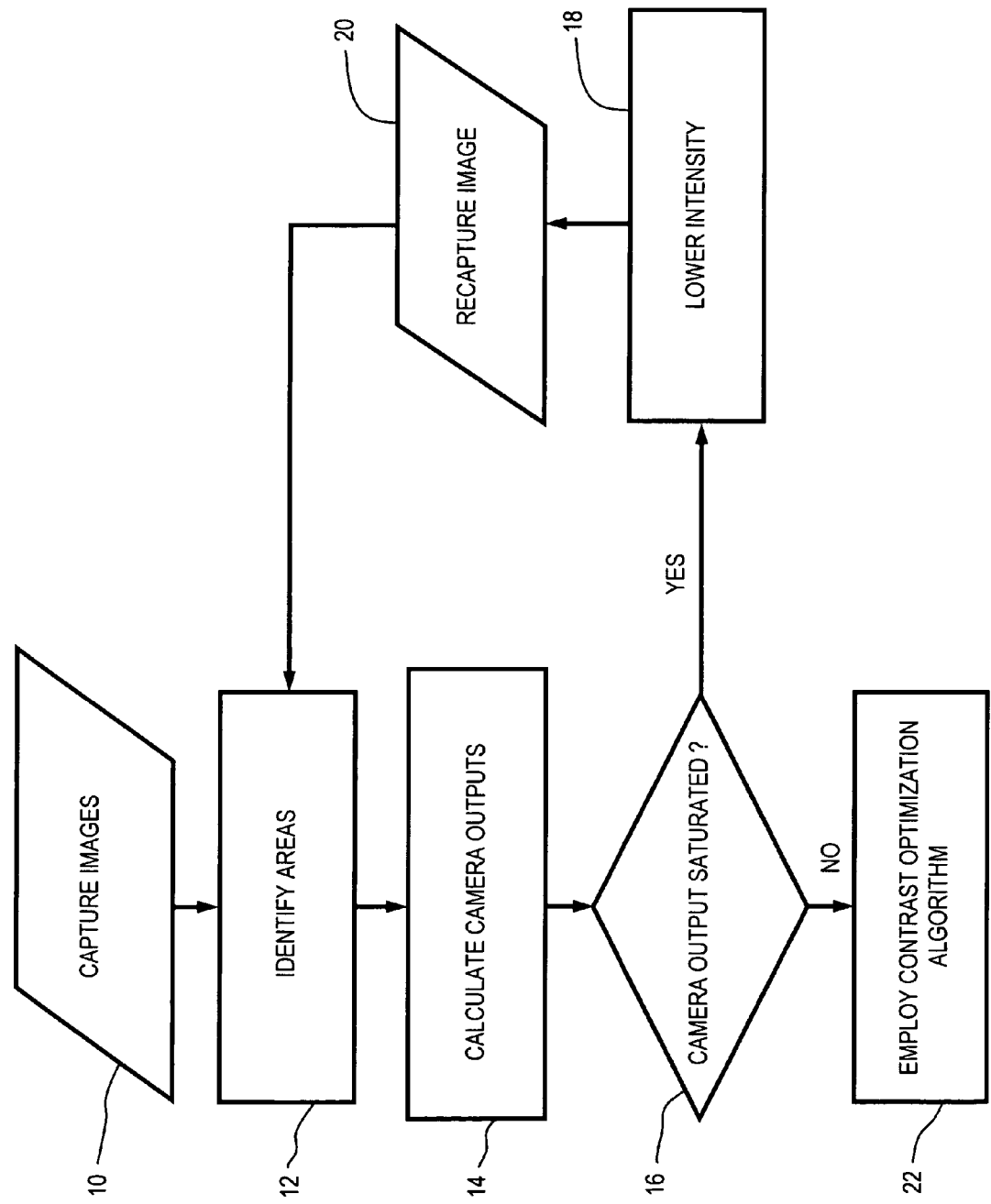
FIG. 4 is a flow chart of contrast optimization according to one aspect of the invention.

The algorithm for determining the optimal lighting conditions for maximum contrast requires knowledge of the camera output for the target and background for all wavelengths available in the multi-wavelength lighting configuration. These conditions can be met by performing the following algorithm described with respect to FIG. 4.

For each wavelength available in the light configuration, an image is captured containing the target and the background at 10. At 12, within these images, two small "target-only" or "background-only" areas are identified. In practice, the easiest way to do so would be to draw two bounding boxes for each area. Next, at 14, the camera outputs for the background and target at each wavelength are calculated by averaging the pixel values for the corresponding areas identified at 12 and factoring out the particular intensity level ($\alpha$) used while capturing that image. If the camera output is saturated for any of the data set at 16, intensity of the lighting is lowered for that image at 18, and the image is recaptured at 20. The algorithm then returns to identify the areas at 12 for the new image and continues through the calculations at 14, or optionally, returns to the calculations at 14 directly. At 22, the contrast optimization algorithm is employed to determine the lighting wavelength that would yield the maximum contrast as well as the proper intensity level that will drive the camera output to the saturation limit for either the background or target area. Note that, as described before, this will help improve the signal-to-noise ratio of the raw image.

Figure 5:
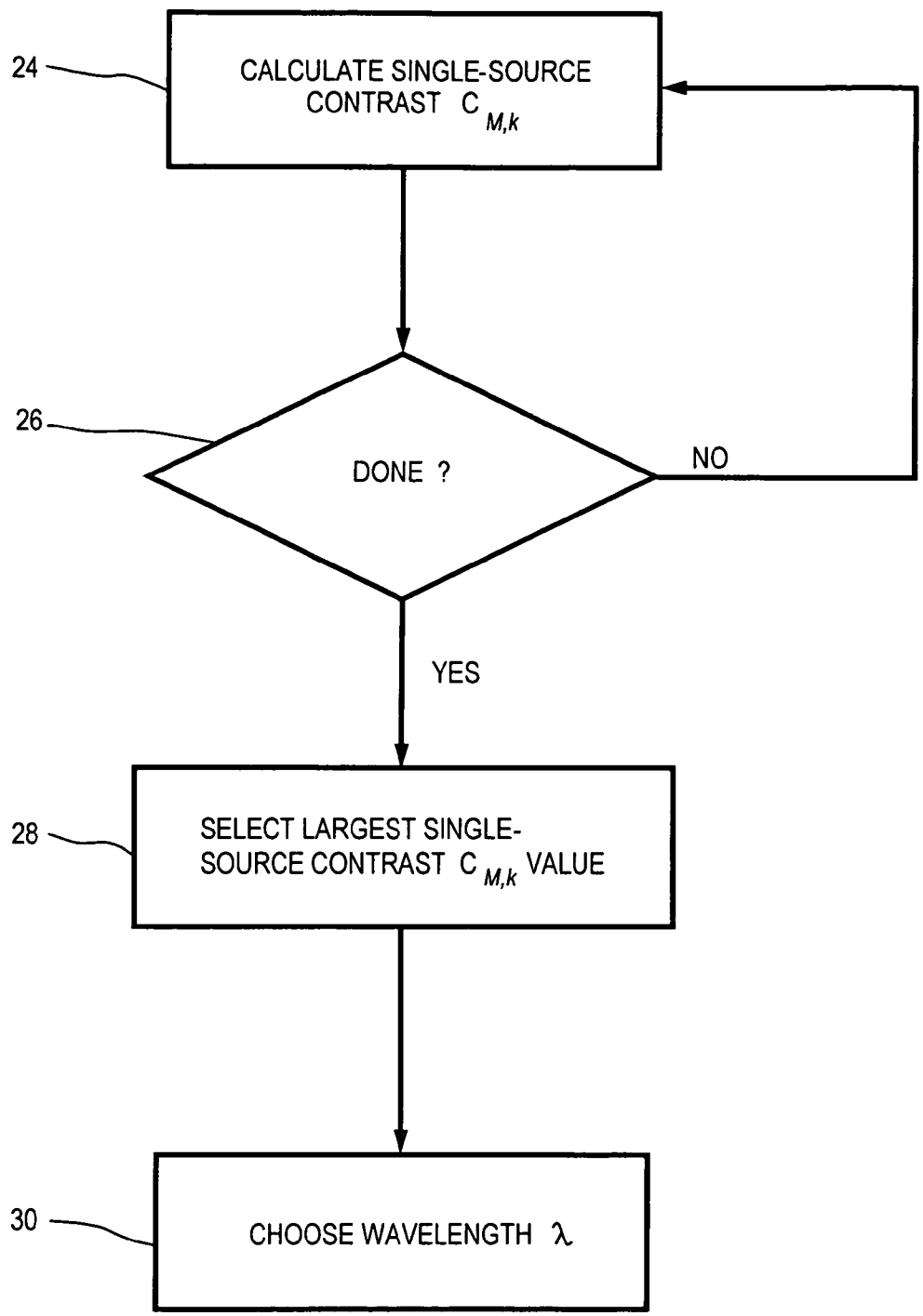
FIG. 5 is a flow chart of details of Block 50 of the contrast optimization shown in FIG. 4.

The contrast optimization algorithm performed at 22 was described previously and can be summarized as shown in FIG. 5. More specifically, at 24 the single-source contrast $C_{M,k}$ for a single source is calculated. At 26 an inquiry is made as to whether the single-source contrast $C_{M,k}$ has been calculated for each source. The calculation at 24 is repeated until all calculations are made. At 28 the largest single-source contrast $C_{M,k}$ is selected. At 30 the wavelength $\lambda_k$ that corresponds to the largest single-source contrast $C_{M,k}$ is chosen to illuminate the surface to obtain image(s) for additional processing.

The disclosure thus far has focused on the determination of the lighting scheme that would yield a single image with the highest contrast between the target and background. Additional benefits can be obtained by utilizing multiple images to create a "composite" image based on data collected under different lighting schemes to improve the performance of a subsequent target identification algorithm, that is, an algorithm known from the prior art that uses an image, such as the optimized or composite image described herein, to identify the target, e.g., indicia. A method to utilize these multiple images is next described.

First, if one had targets and backgrounds that were perfectly uniform in space one could create an image with perfect contrast under virtually any lighting condition. A threshold value that falls between the camera outputs for the target and background would be determined and then binary thresholding would be applied to the raw image to create a black-and-white image with perfect contrast. There are two main reasons why this simplistic approach often fails in practice. One reason is that either the background or the target or both are seldom perfectly uniform in space. Many times they are textured/speckled, which makes the determination of a threshold value to cleanly "split" the target from the background quite difficult. Another reason is that there is always some blurring of the edges, either due to optical limitations or the spatial resolution of the process utilized to create the target against the background.

One response to these problems is to improve the signal-to-noise ratio (SNR) of such an imperfect image. One way to do so is to pick a lighting scheme that maximizes the difference between the target and background images by choosing an illumination wavelength to which the target and background respond differently. This is what the contrast optimization method discussed above does.

Another approach to improving SNR is active noise cancellation. Within the context of target identification from images, this would correspond to eliminating the texture information from the raw image to end up with "smooth" targets and backgrounds. To understand what this might entail under single wavelength illumination, the camera output model from above is generalized to include texture information as follows:

$$\text{Cout}_T(x, y) = T(x, y)U_T(x, y)\alpha_k\Gamma_k^T; \text{ and} \quad (7)$$

$$\text{Cout}_B(x, y) = T(x, y)U_B(x, y)\alpha_k\Gamma_k^B; \quad (8)$$

where the function $T(x,y)$ represents the texture information throughout the entire image, and $U_T(x,y)$ and $U_B(x,y)$ are masking functions that are zero everywhere but over the target and background areas, respectively.

Figure 6:
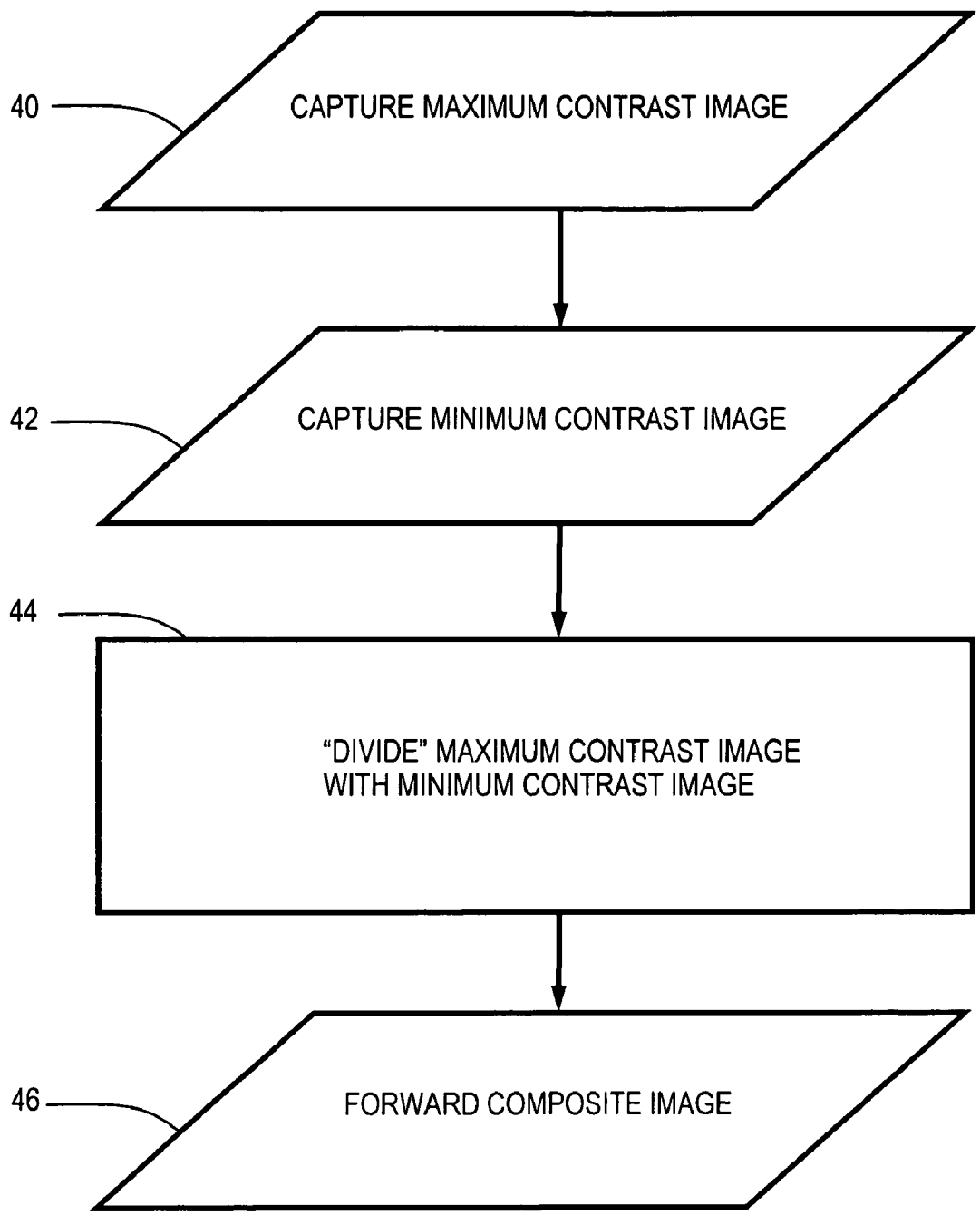
FIG. 6 is a flow chart of the active noise cancellation according to another aspect of the invention.
Figure 7:
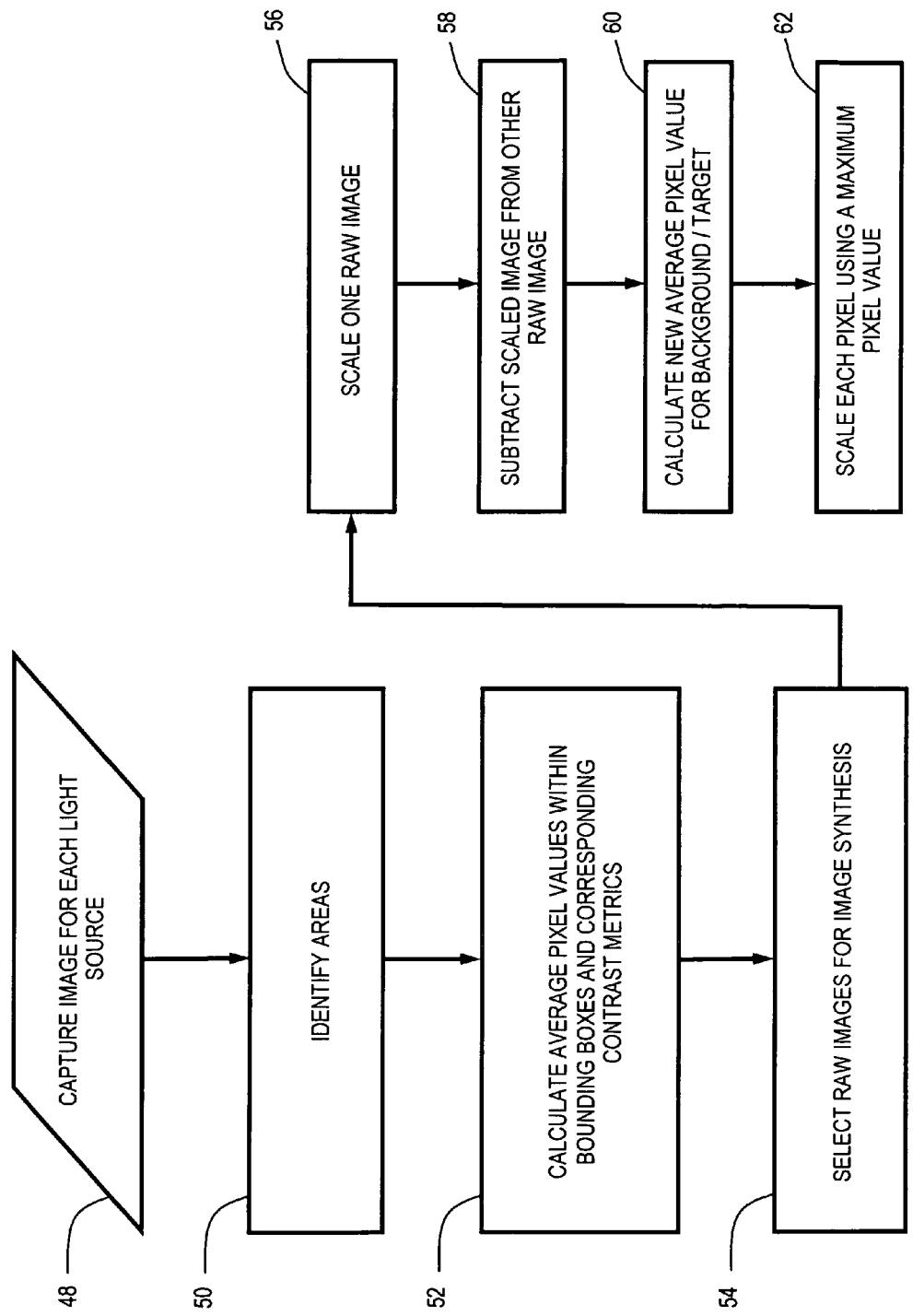
FIG. 7 is a flow chart showing the synthesis of two images.

To use this approach, one obtains two images instead of one. As shown in FIG. 6 at 40, a first image is captured using a wavelength that maximizes the contrast as detailed above in the method for determining the optimal lighting conditions. At 42, the second image is captured using a lighting scheme having a wavelength that minimizes the contrast using the same procedure used to solve the contrast maximization problem above.

By definition, there is minimal target-background differentiation information in an image captured via a lighting scheme that minimizes the contrast between the target (or fiducial) and the background. Consequently, the minimal contrast image mainly contains texture data that this method is attempting to eliminate. Thus, at 44, the image with maximum contrast is "divided" by the one with the minimal contrast to effectively cancel out the T(x,y) terms from equations (7) and (8). That is, a brightness value for each pixel of the image is divided by a brightness value for the corresponding pixel in the image with the minimal contrast. This results in a much smoother, i.e., relatively noise-free, image of background and target. This so-called "composite" image can then be fed at 46 into the downstream target identification algorithm for processing as described previously.

A third approach to improving the SNR of an image is to form a synthetic image of the area of interest from a plurality images captured when a target and background are illuminated by each of two or more wavelengths. In this example, one image is subtracted from another to create a synthetic image with enhanced contrast between the target and the background.

More specifically, consider the scenario discussed above with respect to RGB lighting with the following observed $\Gamma$ values:

$$\Gamma_R^T=5, \Gamma_R^B=2;$$

$$\Gamma_G^T=3, \Gamma_G^B=5;$$

$$\Gamma_B^T=8, \Gamma_B^B=5.$$

According to the previous discussion, red lighting alone would give the highest contrast raw image. Consider, however, a synthetic image obtained by subtracting the image obtained under green lighting from that obtained under blue lighting. This is equivalent to setting the intensities $\alpha_R=0$, $\alpha_G=-1$ and $\alpha_B=+1$. Substituting these values in equation (5), we find that the contrast metric for the synthetic image is 1, which is much higher than what we could achieve with the optimal raw image obtained with red-only lighting.

Two important aspects of the example above deserve to be highlighted. First, the image resulting from subtraction of one raw image from the other is truly "synthetic." Trying to generate such an image physically through lighting modifications would require "negative" intensities, which are not physically possible. Second, it will always be possible through scaling and subtraction of raw images to obtain a synthetic image with unity contrast metric: all one has to do is to scale individual images so that they either "match" in target area or background area, and then subtract one (scaled) image from the other.

Figure 8:
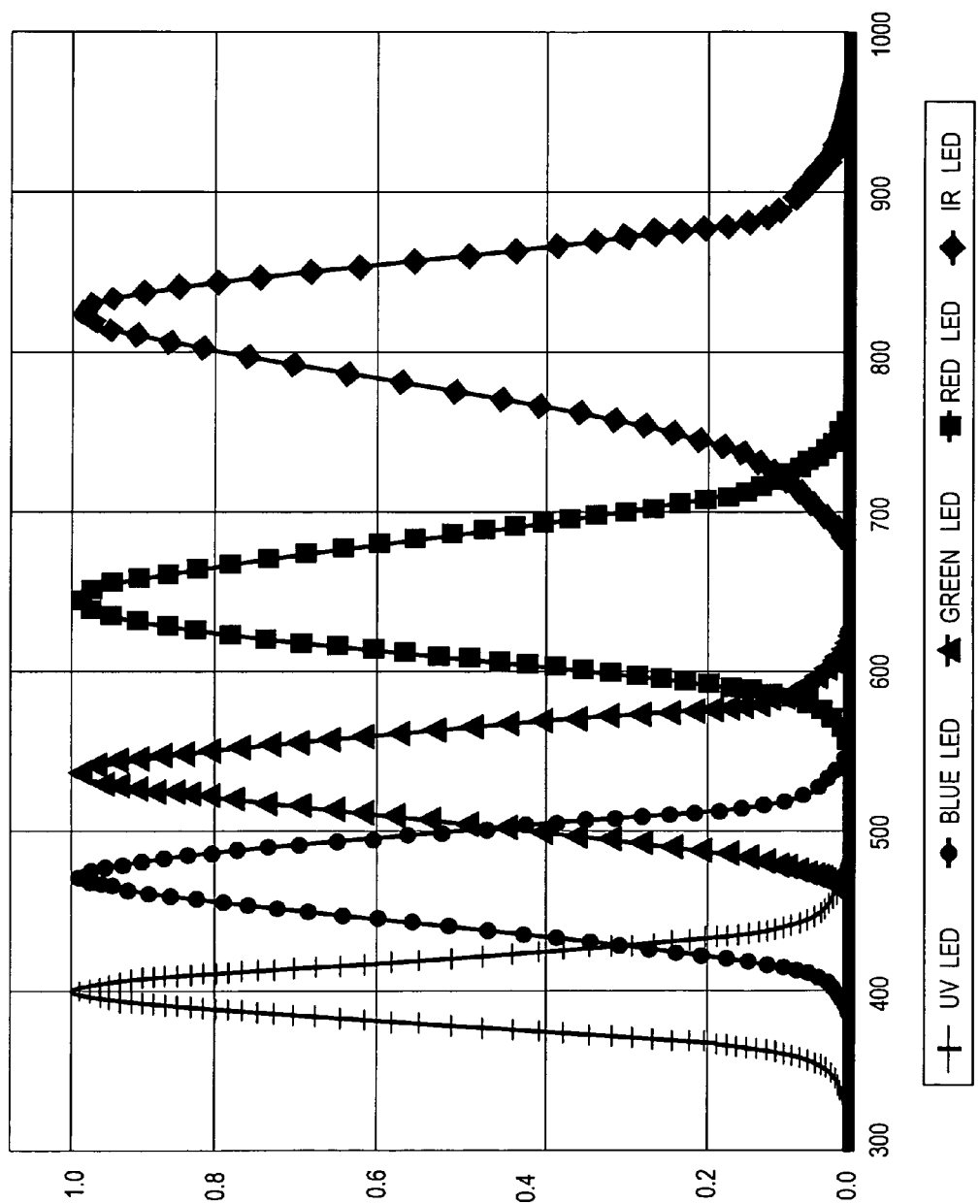
FIG. 8 is graph showing typical spectral outputs of the multi-color LEDs described herein.

An actual example of the teachings above is shown with reference to FIGS. 7-11. In this example, an alignment target on a PCB board is illuminated using blue, green, red and infrared LEDs, and the corresponding four "raw" images are captured by the monochromatic camera at 48. FIG. 8 shows the spectral outputs of the multi-color LEDs described. The resulting raw images can be seen in FIGS. 9A through 9D where FIG. 9A shows the target and background under blue LED illumination, and FIGS. 9B-9D show the same target and background under green LED illumination, red LED illumination and infrared (IR) LED illumination, respectively.

Figure 9A:
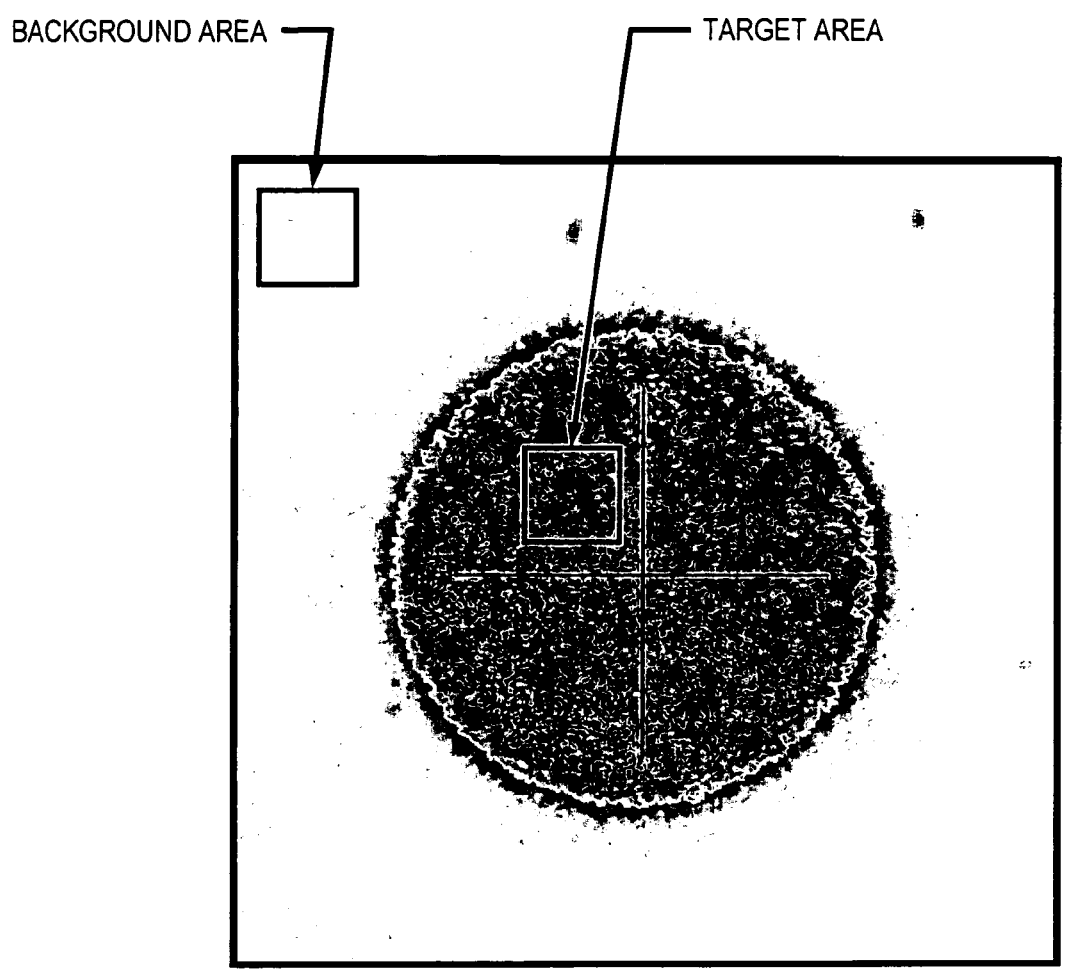
FIG. 9A is a raw image of an actual alignment target captured by a monochromatic camera under blue LED illumination, and the bounding boxes for "target" and "background" areas of the image.
Figure 9B:
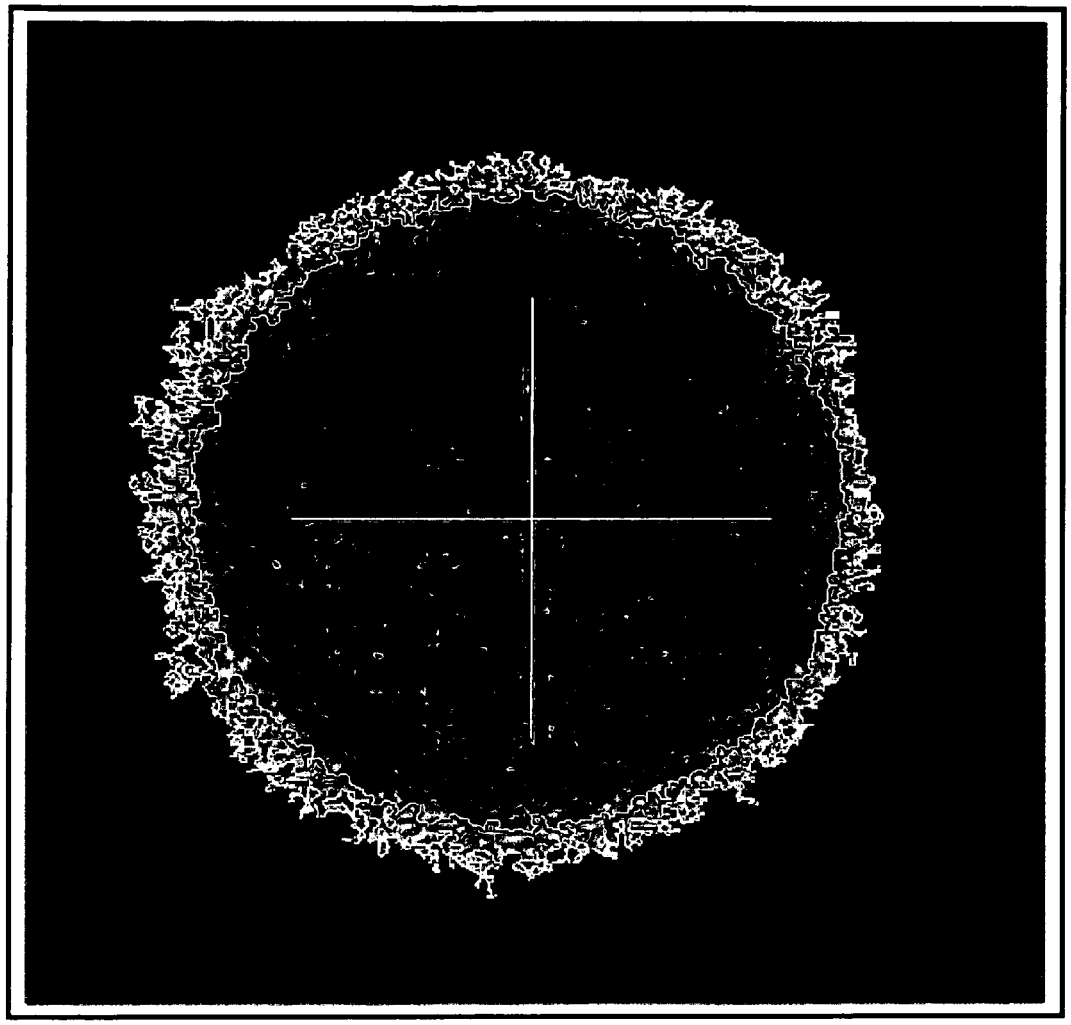
FIG. 9B is a raw image of the same alignment target captured by the same monochromatic camera under green LED illumination.
Figure 9C:
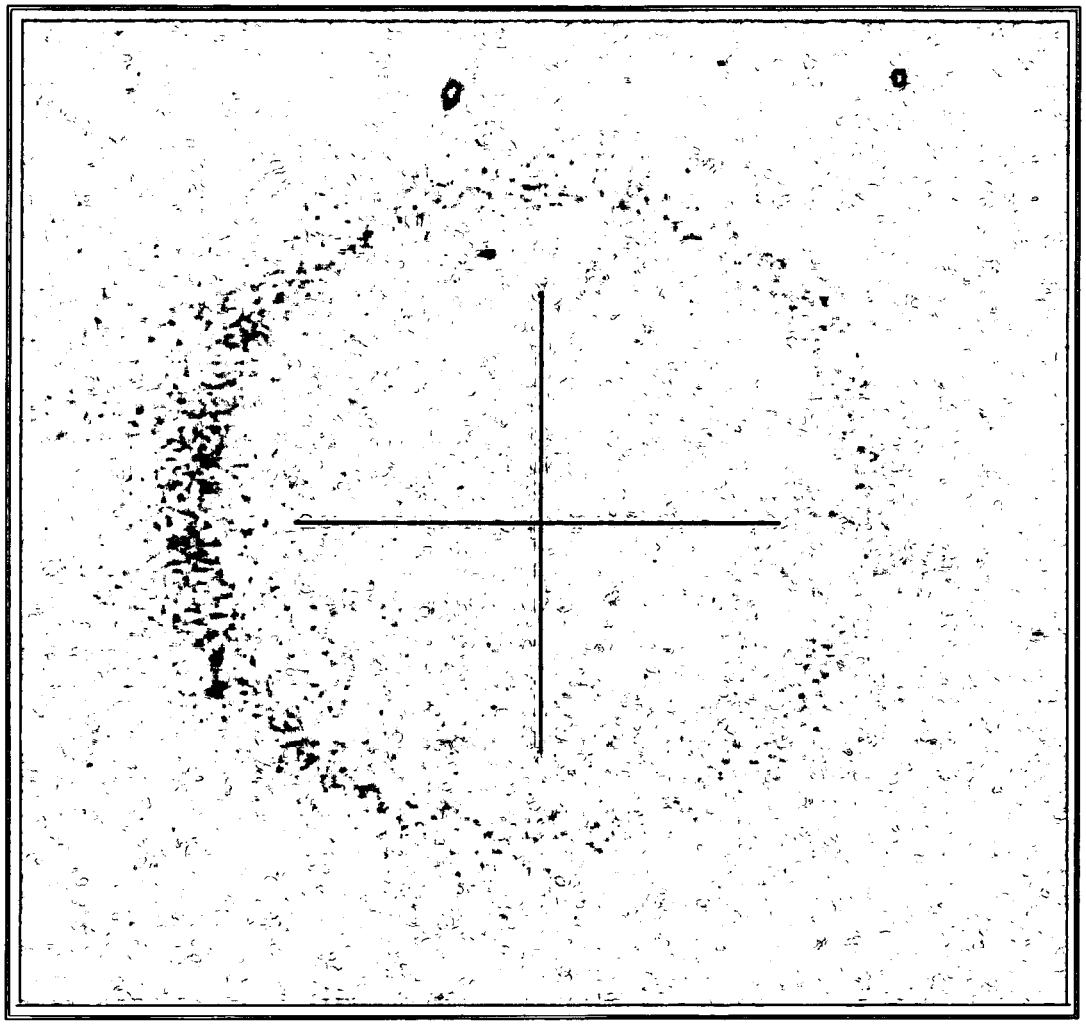
FIG. 9C is a raw image of the same alignment target captured by the same monochromatic camera under red LED illumination.
Figure 9D:
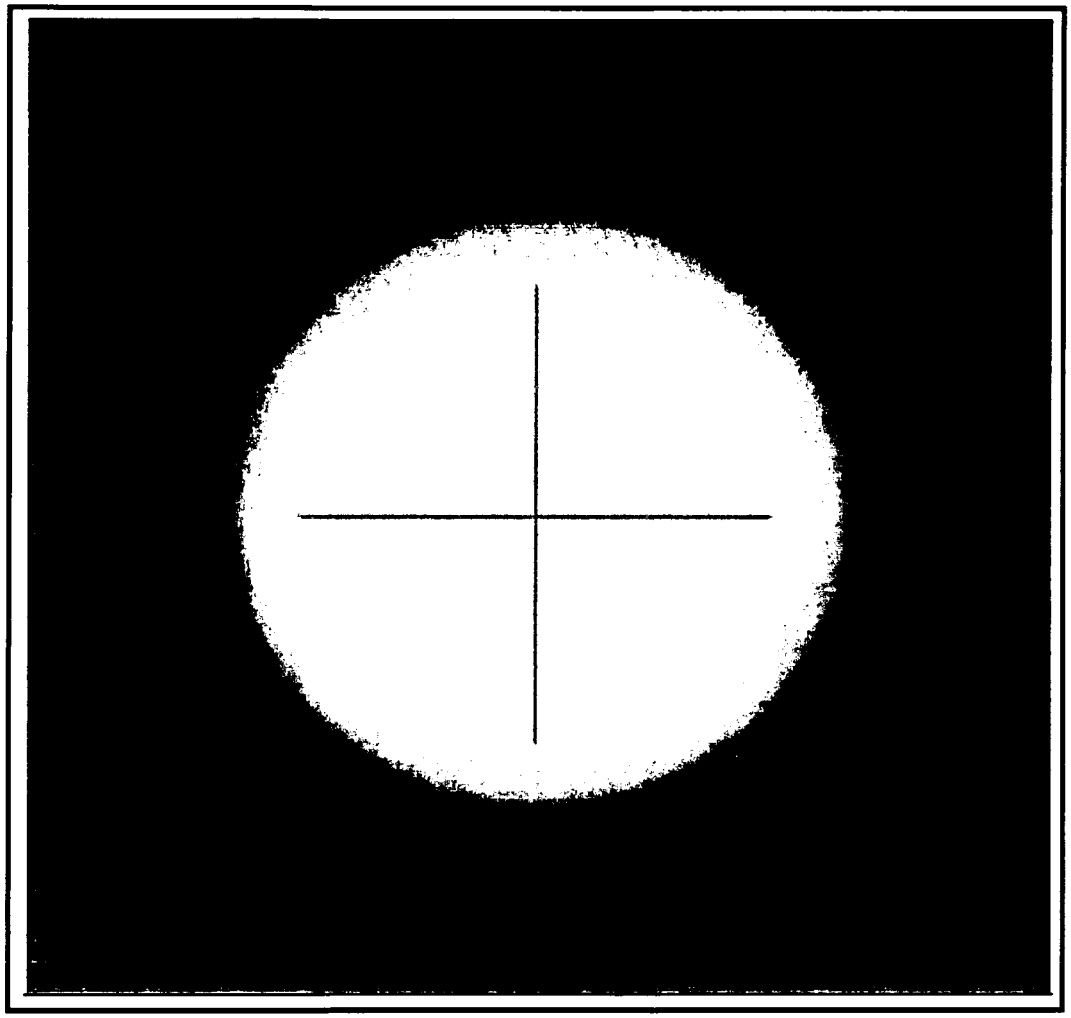
FIG. 9D is a raw image of the same alignment target captured by the same monochromatic camera under infrared (IR) LED illumination.

Next, bounding boxes for "target" and "background" areas of the image are determined for each raw image at 50. Examples of these bounding boxes are shown in FIG. 9A. Average pixel values within these bounding boxes are calculated for all four images and the corresponding contrast metrics are determined at 52. The results of these calculations are summarized in FIG. 10. According to these results, the raw image obtained under blue LED illumination has the highest contrast between the target and the background. This is consistent with the visual comparison of the four images.

A "synthesized" image can be obtained in the following manner. First, the images to be used for the synthesized image using algebraic manipulation are selected at 54. In this example, the first image selected is the raw image obtained under blue LED illumination, and the second image selected is the raw image obtained under IR LED illumination. These raw images have an inverted ratio between their respective background and target average pixel values with respect to each other. Next, one of the images is scaled so that the average pixel value for either the background or the target can be "zeroed" out at 56. In this case for example every pixel of the raw image obtained under IR LED illumination is multiplied by the ratio of the target average pixel value of the raw image obtained under blue LED illumination by the target average pixel value of the raw image obtained under IR LED illumination, i.e., 144.1300/125.7639.

The scaled image is subtracted pixel-by-pixel from the other selected image, here the raw image obtained under blue LED illumination, at 58. This results in an image that has virtually zero (0) average pixel value for the target area. For the resulting image, the average pixel value for the area not zeroed out is next calculated at 60. For this example image, the average background pixel value is calculated. Then, at 62 each pixel of the image is scaled by a proper factor to bring the average pixel value, here the average pixel value for the background area, up to a maximum pixel value such as 255.

Figure 11:
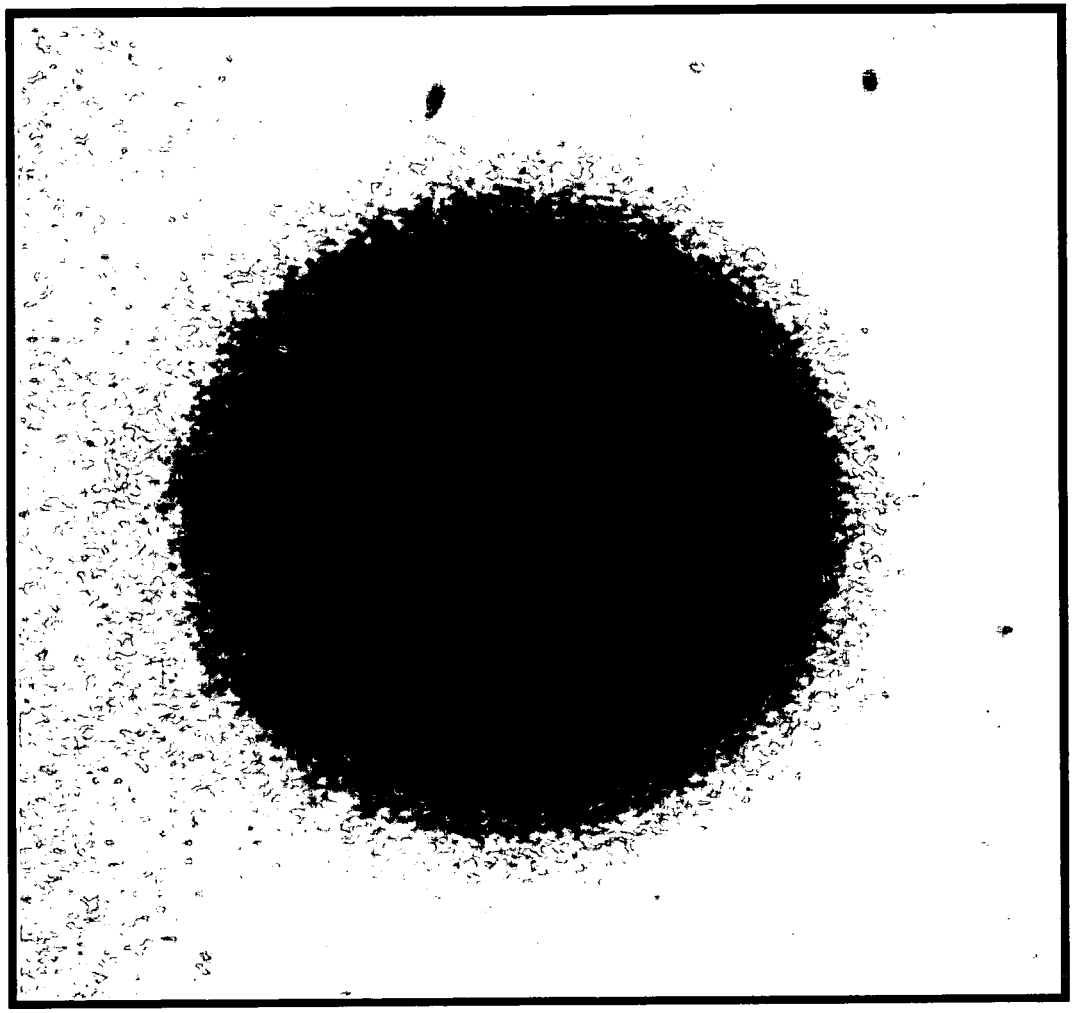
FIG. 11 is the synthesized contrast image obtained by algebraically combining the raw images of FIGS. 9A and 9D obtained under blue and IR LED illumination according to the flow chart of FIG. 7.

The synthetic image after performing these steps is illustrated in FIG. 11. The contrast metric for this image has been calculated as 0.9624, which is very close to the theoretical maximum of 1. This contrast metric marks a significant improvement in contrast compared to the four raw images as shown in FIG. 10. This improvement is also easily verified by visual inspection of the image as shown in FIG. 11.

The above-described embodiments have been described in order to allow easy understanding of the present invention, and do not limit the present invention. On the contrary, the invention is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A method to improve image quality in images of a surface captured via a monochromatic camera, the surface including a target and a background, the method comprising:
    using multi-wavelength lighting to obtain a plurality of images including:
        varying the multi-wavelength lighting among a plurality of wavelengths; and
        obtaining an image at each of the plurality of wavelengths; and
    optimizing contrast between portions of the surface based on the plurality of images including determining which wavelength among the plurality of wavelengths results in an image having an optimum contrast.

2. The method according to claim 1 wherein optimizing contrast comprises:
calculating a single-source contrast value for each image; and wherein determining which wavelength among the plurality of wavelengths results in an image having an optimum contrast comprises choosing a wavelength corresponding to a largest single-source contrast value.

3. The method according to claim 1, further comprising: algebraically combining at least two images to synthesize a high contrast composite image.

4. The method according to claim 1, further comprising:
capturing a first image using the contrast obtained when optimizing contrast of the multi-wavelength lighting;
minimizing contrast of the multi-wavelength lighting using the plurality of images;
capturing a second image using the contrast obtained when minimizing contrast of the multi-wavelength lighting; and
comparing the first image to the second image to reduce a signal-to-noise ratio.

5. The method according to claim 4 wherein comparing the first image to the second image further comprises performing a pixel-by-pixel division of brightness data of the first image by brightness data of the second image.

6. A method to improve image quality in images of a surface captured via a monochromatic camera, the surface including a target and a background, the method comprising:
using multi-wavelength lighting to obtain a plurality of images;
optimizing contrast between portions of the surface based on the plurality of images;
determining a respective camera output for the target and the background for each wavelength of the multi-wavelength lighting; and
using the respective camera output for the target and the background when optimizing contrast.

7. The method according to claim 6 wherein determining the respective camera output for the target and the background comprises:
capturing an image for a wavelength of the multi-wavelength lighting;
identifying at least two target areas within a target-only area;
identifying at least two background areas within a background-only area;
averaging pixel values for the at least two target areas;
averaging pixel values for the at least two background areas;
factoring out an intensity level used while capturing the image.

8. The method according to claim 7, further comprising: lowering the intensity level and re-capturing the image when the camera output indicates at least one of the target and the background is saturated.

9. The method according to claim 7 wherein optimizing contrast between portions of the surface comprises:
calculating a single-source contrast for the surface for each wavelength of the plurality of wavelengths available in the multi-wavelength lighting; and
choosing the wavelength that corresponds to the largest single-source contrast value.

10. The method according to claim 6, further comprising: performing a pixel-by-pixel division of a maximum contrast image by a minimum contrast image to create a composite image with a reduced signal-to-noise ratio.

11. An apparatus to improve image quality in images of a surface captured via a monochromatic camera, the surface including a target and a background, the apparatus comprising:
means for using multi-wavelength lighting to obtain a plurality of images, the means for using multi-wavelength lighting including:
means for varying the multi-wavelength lighting among a plurality of wavelengths; and
means for obtaining an image at each of the plurality of wavelengths;
means for algebraically combining at least two images to synthesize a high contrast composite image; and
means for optimizing contrast between portions of the surface based on the plurality of images.

12. The apparatus according to claim 11 wherein the means for optimizing contrast comprises:
means for calculating a single-source contrast value for each image; and
means for choosing a wavelength corresponding to a largest single-source contrast value.

13. The apparatus according to claim 11 wherein the means for algebraically combining at least two images comprises:
means for selecting a first one of the images;
means for selecting a second one of the images;
means for scaling one the first one of the images to obtain a scaled image and for subtracting the scaled image from the second one of the images to obtain a third image wherein a contrast of one of the background and the target of the third image is about zero; and
means for scaling each pixel of the third image to obtain a maximum average pixel value wherein a resulting image is the high contrast composite image.

14. The apparatus according to claim 13, further comprising:
means for calculating an average pixel value of the other of the background and the target of the third image; and
wherein the means for scaling each pixel of the third image uses the average pixel value.

15. An apparatus to improve image quality in images of a surface captured via a monochromatic camera, the surface including a target and a background, the apparatus comprising:
means for using multi-wavelength lighting to obtain a plurality of images;
means for optimizing contrast between portions of the surface based on the plurality of images;
means for using the contrast obtained when optimizing contrast of the multi-wavelength lighting to capture a first image;
means for minimizing contrast of the multi-wavelength lighting using the plurality of images;
means for using the contrast obtained when minimizing contrast of the multi-wavelength lighting to capture a second image; and
means for comparing the first image to the second image to reduce a signal-to-noise ratio.

16. The apparatus according to claim 15 wherein the means for comparing the first image to the second image further comprises means for performing a pixel-by-pixel division of brightness data of the first image by brightness data of the second image.

* * * * *